United States Patent
Rahbar (12) 
(10) Patent No.: US 6,589,944 B1
(45) Date of Patent: Jul. 8, 2003

(54) BREAKERS OF ADVANCED GLYCATION ENDPRODUCTS

(75) Inventor: Samuel Rahbar, Encino, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/626,859

(22) Filed: Jul. 27, 2000

Related U.S. Application Data (63) Continuation-in-part of application No. 09/559,913, filed on Apr. 28, 2000, now abandoned, which is a continuation-in-part of application No. 09/543,703, filed on Apr. 5, 2000, now Pat. No. 6,337,350.
(60) Provisional application No. 60/131,675, filed on Apr. 29, 1999, and provisional application No. 60/127,835, filed on Apr. 5, 1999.

(51) Int. Cl.$^7$ ................. A61K 31/155; A61K 31/195; A01N 37/36
(52) U.S. Cl. ................. 514/166; 514/562; 514/563; 514/564; 514/567; 514/635; 514/866; 514/878
(58) Field of Search ................. 514/166, 635, 514/562, 563, 564, 567, 866, 878

(56) References Cited

U.S. PATENT DOCUMENTS 4,880,794 A * 11/1989 Halskov .................. 514/166

FOREIGN PATENT DOCUMENTS

| WO | WO 92/07560 A1 | 5/1992 |
| WO | WO 92/07560 | * 5/1992 |
| WO | WO 00/66102 A2 | 11/2000 |

OTHER PUBLICATIONS

S. Rahbar et al., "Novel Inhibitors of Advanced Glycation Endproducts," Biochemical and Biophysical Research Communications 262:651–656, 1999.
S. Rahbar et al., "A new rapid method to detect inhibition of Amadori product generated by δ–gluconolactone," Clinica Chimica Acta 287:123–130, 1999.
Asif, M. et al. "An advanced glycation endproduct cross–link breaker can reverse age–related increases in myocardial stiffness", PNAS, Mar. 14, 2000; 97(6):2809–2813 plus 1 page with correction.
Beisswenger, P.J. et al. "Metformin Reduces Systemic Methylglyoxal Levels in Type 2 Diabetes", Diabetes, Jan. 1999; 48:198–202.
Cooper, M.E. et al. "The cross–link breaker, N–phenacylthiazolium bromide prevents vascular advanced glycation end–product accumulation", Diabetologia, 2000; 43:660–664.
Jyothirmayi, G.N. et al. "Effects of Metformin on Collagen Glycation and Diastolic Dysfunction in Diabetic Myocardium", J. Cardiovasc. Pharmacol. Therapeut., 1998; 3(4):319–326.
Lalezari, I. et al. "Synthesis and Investigation of Effects of 2–[4–[[(Arylamino)carbonyl]amino]phenoxy]–2–methyl-propionic Acids on the Affinity of Hemoglobin for Oxygen: Structure–Activity Relationships", J. Med. Chem., 1989; 32:2352–2357.
Lalezari, I. et al. "LR16, a compound with potent effects on the oxygen affinity of hemoglobin, on blood cholesterol, and on low density lipoprotein", Proc. Natl. Acad. Sci. USA, Aug. 1988; 85:6117–6121.
Rahbar, S. et al. "A new rapid method to detect inhibition of Amadori product generated by δ–gluconolactone", Clinica Chimica Acta, 1999; 123–130.
Rahbar, S. et al. "Novel Inhibitors of Advanced Glycation Endproducts", Biochemical and Biophysical Research Communications, 1999; 262:651–656.
Raj, D.S.C. et al. "Advanced Glycation End Products: A Nephrologist's Perspective", American Journal of Kidney Diseases, Mar. 2000, 35(3):365–380.
Ruggiero–Lopez, D. et al. "Reaction of Metformin with Dicarbonyl Compounds. Possible Implication in the Inhibition of Advanced Glycation End Product Formation", Biochemical Pharmacology, 1999; 58:1765–1773.
Tanaka, Y. et al. "Effect of metformin on advanced glycation endproduct formation and peripheral nerve function in streptozotocin–induced diabetic rats", European Journal of Pharmacology, 1999; 376:17–22.
Thornalley, P.J. et al. "Rapid Hydrolysis and Slow α,β–Dicarbonyl Cleavage of an Agent Proposed to Cleave Glucose–Derived Protein Cross–Links", Biochemical Pharmacology, 1999; 57:303–307.
Ulrich, P. et al. "Pharmacological reversal of advanced glycation end–product–mediated protein crosslinking", Diabetologia, 1997; 40:S157–S159.
Vasan, S. et al. "An agent cleaving glucose–derived protein crosslinks in vitro and in vivo", Nature, Jul. 18, 1996; 382:275–278.
Wolffenbuttel, B.H.R. et al. "Breakers of advanced glycation end products restore large artery properties in experimental diabetes", Proc. Natl. Acad. Sci. USA, Apr. 1998; 95:4630–4634.

* cited by examiner

Primary Examiner—Frederick Krass
(74) Attorney, Agent, or Firm—Rothwell, Figg, Ernest & Manbeck (57) ABSTRACT

Advanced glycation endproducts (AGEs) have been implicated in the pathogenesis of a variety of debilitating diseases such as diabetes, atherosclerosis, Alzheimer's and rheumatoid arthritis, as well as in the normal aging process. Five compounds are here reported to be active in breaking AGE-protein cross-links. These compounds are L-bis-[4-(4-chlorobenzamido-phenoxyisobutyryl)cystine] (LR20); 4-(3,5-dichlorophenylureido)phenoxyisobutyryl-1-amido-cyclohexane-1-carboxylic acid (LR23); methylene bis [4,4'-(2-chlorophenylureido-phenoxyisobutyric acid)] (LR90); 5-arninosalicylic acid (5-ASA); and metformin. These compounds may be used to reverse the debilitating effects of those diseases in which AGEs are formed.

4 Claims, 3 Drawing Sheets

BREAKERS OF ADVANCED GLYCATION ENDPRODUCTS

CROSS REFERENCE TO RELATED APPLICATIONS

The present invention is a continuation-in-part of application Ser. No. 09/543,703 filed Apr. 5, 2000 now U.S. Pat. No. 6,337,350, which is related to application Ser. No. 60/127,835 filed Apr. 5, 1999, and is a continuation-in-part of application Ser. No. 09/559,913 filed April 28, 2000 now abandoned, which is related to application Serial No. 60/131,675 filed 29 April 1999, all of which are incorporated herein by reference.

BACKGROUND OF THE INVENTION

Glucose and other reducing sugars react and bind covalently to proteins, lipoproteins and DNA by a process known as non-enzymatic glycation. Glucose latches onto tissue proteins by coupling its carbonyl group to a side-chain amino group such as that found on lysine. Over time, these adducts form structures called advanced glycation endproducts (AGEs) (protein-aging). These cross-linked proteins stiffen connective tissue and lead to tissue damage in the kidney, retina, vascular wall and nerves. The formation of AGEs on long-lived connective tissue accounts for the increase in collagen cross-linking that accompanies normal aging which occurs at an accelerated rate in diabetes.

The publications and other materials used herein to illuminate the background of the invention or provide additional details respecting the practice, are incorporated by reference, and for convenience are respectively grouped in the appended List of References.

Advanced glycation endproducts (AGEs) have been implicated in the pathogenesis of a variety of debilitating diseases such as diabetes, atherosclerosis, Alzheimer's and rheumatoid arthritis, as well as in the normal aging process. Most recent researchers confirm a significant role of the accumulation of AGE cross-links in promoting the decreased cardiovascular compliance of aging (Asif et al., 2000). The process of AGE formation on arterial wall matrix proteins may be related to the development of atherosclerosis in many different ways, such as generation of free radicals (ROS) during the glycation process, inhibition of a normal network formation in collagen by AGE accumulation (Brownlee, 1994), and increased adhesion of monocytes (Gilcrease and Hoover, 1992).

The hallmark Diabetes Control and Complications Trial (DCCT) demonstrated that normalization of blood glucose control by intensive insulin therapy reduces the risk of development of diabetic complications (Diabetes Control and Complications Trial Research Group, 1993). However, intensive insulin therapy neither prevents nor cures complications. Thus, a large number of patients still are prone to develop vascular complications, and additional pharmacological approaches to prevent these complications are desirable.

Both inhibitors of AGE formation and AGE-breakers not only may have a beneficial effect in reducing these complications, AGE-breakers may cure the disease by removing AGEs from damaged tissues and cells.

A large number of inhibitors of glycation, AGE-formation and AGE-protein cross-linking have been reported recently by us and others. Aminoguanidine is a prototype of "glycation inhibitors". These inhibitors may find therapeutic use in preventing diabetic complications and in delaying normal aging.

In addition to aminoguanidine, a large number of much more potent inhibitor compounds have been introduced by us and others recently (Rahbar et al., 1999; Rahbar et al., 2000a; Rahbar et al., 2000b; Kochakian et al., 1996; Khalifah et al., 1999). On the other hand, investigation for selectively cleaving and severing the existing AGE-derived cross-links on tissue proteins by pharmacological strategies has been started more recently. N-phenacylthiazolium bromide (PTB) and ALT 711 have been reported to have the ability to break AGE cross-links in vitro and in vivo. The introduction of PTB, the first AGE-breaker which was introduced in 1996, generated excitement among the researchers in this field. However, PTB which was used at high concentrations (10–30 mM), was only active at non-physiological high levels (Thomalley and Minhas, 1999). ALT 711 has demonstrated AGE-breaking activities both in vitro and in vivo (Vasan et al., 1996). Yang et al. (2000) studied the effects of ALT 711 in reversing the increase in cross-linking of skin collagen in STZ induced diabetic rats. They concluded that ALT 711 is not effective in cleaving cross-links formed in skin collagen of diabetic rats. The search for new AGE-breaker compounds to prevent and cure disease related to AGE accumulation in tissues and organs is warranted.

The Diabetes Control and Complications Trial (DCCT), has identified hyperglycemia as the main risk-factor for the development of diabetic complications (Diabetes Control and Complications Trial Research Group, 1993). Ever increasing evidence identifies the formation of advanced glycation endproducts (AGEs) as the major pathogenic link between hyperglycemia and the long-term complications of diabetes, namely nephropathy, neuropathy and retinopathy (Makita et al., 1994; Koschinsky et al., 1997; Makita et al., 1993; Bucala et al., 1994; Bailey et al., 1998).

Nonenzymatic glycation is a complex series of reactions between reducing sugars and amino groups of proteins, lipids and DNA, which lead to browning, fluorescence, and cross-linking (Bucala and Cerami, 1992; Bucala et al., 1993; Bucala et al., 1984). The reaction is initiated with the reversible formation of a Schiff's base, which undergoes a rearrangement to form a stable Amadori product. Both the Schiff's base and Amadori product further undergo a series of reactions through dicarbonyl intermediates to form advanced glycation endproducts (AGEs).

In human diabetic patients and in animal models of diabetes, these nonenzymatic reactions are accelerated and cause accumulation of glycation and AGE formation on long-lived structural proteins such as collagen, fibronectin, tubulin, lens crystallin, myelin, laminin and actin, and in addition on hemoglobin, albumin, LDL associated lipids and apoprotein. Most recent reports indicate that glycation inactivates metabolic enzymes (Yan and Harding, 1999). The structural and functional integrity of the affected molecules, which often have major roles in cellular functions, become perturbed by these modifications with severe consequences on affected organs such as kidney, eye, nerve, and microvascular functions (Boel et al., 1995; Silbiger et al., 1993). The glycation-induced change of immunoglobin G is of particular interest. Recent reports of glycation of Fab fragment of IgG in diabetic patients suggest that immune deficiency observed in these patients may be explained by this phenomenon (Lapolla et al., 2000). Furthermore, an association between IgM response to IgG damaged by glycation and disease activity in rheumatoid arthritis have been reported recently (Lucey et al., 2000). Also, impairment of high-density lipoprotein function by glycation has been reported recently (Hedrick et al., 2000).

Direct evidence indicating the contribution of AGEs in the progression of diabetic complications in different lesions of the kidneys, the rat lens, and in atherosclerosis has been recently reported (Vlassara et al., 1995; Horie et al., 1997; Matsumoto et al., 1997; Soulis-Liparota et al., 1991; Bucala, 1997; Bucala and Rahbar, 1998; Park et al., 1998). Several lines of evidence indicate the increase in reactive carbonyl intermediates (methylglyoxal, glyoxal, 3-deoxyglucosone, malondialdehyde, and hydroxynonenal) is the consequence of hyperglycemia in diabetes. "Carbonyl stress" leads to increased modification of proteins and lipids, followed by oxidant stress and tissue damage (Baynes and Thorpe, 1999; Onorato et al., 1999; McLellan et al., 1994).

Methylglyoxal (MG) has recently received considerable attention as a common mediator to form AGEs. In patients with both insulin-dependent and non-insulin dependent diabetes, the concentration of MG was found to be increased 2–6 fold (Phillips and Thornalley, 1993; Beisswenger et al., 1998). Furthermore, MG has been found not only as the most reactive dicarbonyl AGE-intermediate in cross-linking of proteins, a recent report has found MG to generate reactive oxygen species (ROS) (free radicals) in the course of glycation reactions (Yim etal., 1995).

An intricate relation between glycation reactions and "oxidative stress" has been postulated. Nature has devised several humoral and cellular defense mechanisms to protect tissues from deleterious effects of "carbonyl stress" and accumulation of AGEs, i.e., the glyoxylase system (I and II) and aldose reductase catalyze the detoxification of MG to D-lactate. Amadoriases are also a novel class of enzymes found in Aspergillus which catalyze the deglycation of Amadori products (Takahashi et al., 1997). Furthermore, several AGE-receptors have been characterized on the surface membranes of monocyte, macrophage, endothelial, mesangial and hepatic cells. One of these receptors, RAGE, a member of the immunoglobulin superfamily, has been found to have a wide tissue distribution (Schmidt et al., 1994; Yan et al., 1997). MG binds to and irreversibly modifies arginine and lysine residues in proteins. MG modified proteins have been shown to be ligands for the AGE receptor (Westwood et al., 1997) indicating that MG modified proteins are analogous (Schalkwijk et al., 1998) to those found in AGEs. Most recently, the effects of MG on LDL have been characterized in vivo and in vitro (Bucala et al., 1993).

Lipid peroxidation of polyunsaturated fatty acids (PUFA), such as arachidonate, also yield carbonyl compounds. Some are identical to those formed from carbohydrates (Al-Abed et al., 1996), such as MG and glyoxal (GO), and others are characteristic of lipid, such as malondialdehyde (MDA) and 4-hydroxynonenal (HNE) (Requena et al., 1997). The latter of the carbonyl compounds produce lipoxidation products (Al-Abed et al., 1996; Requena et al., 1997). A recent report emphasizes the importance of lipid-derived MDA in the cross-linking of modified collagen and in diabetes mellitus (Slatter et al., 2000). A number of AGE compounds, including both fluorophores and nonfluorescent compounds, are involved in cross-linking proteins and have been characterized (Baynes and Thorpe, 1999) (see Table 1). In addition to glucose derived AGE-protein cross-links, AGE crosslinking also occurs between tissue proteins and AGE-containing peptide fragments formed from AGE-protein digestion and turnover. These reactive AGE-peptides, now called glycotoxins, are normally cleared by the kidneys. In diabetic patients, these glycotoxins react with the serum proteins and are a source for widespread tissue damage (He et al., 1999). However, detailed information on the chemical nature of the cross-link structures remains unknown. The cross-linking structures characterized to date (Table 1), on the basis of chemical and spectroscopic analyses, constitute only a small fraction of the AGE-cross-links which occur in vivo, with the major cross-linking structure(s) still unknown. Most recently, a novel acid-labile AGE-structure, N-omega-carboxymethylarginine (CMA), has been identified by enzymatic hydrolysis of collagen, and its concentration was found to be 100 times greater than the concentration of pentosidine (Iijima et al., 2000), and has been assumed to be a major AGE-cross-linking structure.

TABLE 1

CURRENT LIST OF AGEs IDENTIFIED IN TISSUE
PROTEINS AND IN VITRO GLYCATION EXPERIMENTS
(Baynes et al., 1999)

Carboxymethyllysine (CML)
Carboxyethyllysine (CEL)
Carboxymethylarginine (CMA)
Pentosidine
Pyralline
Crosslines (A, B)
Glyoxallysine dimers (GOLD), Imidazolium salts
Methylglyoxal-lysine dimers (MOLD), Imidazolium salts

| Imidazolones and | { | 3-Deoxyglucosone-Arginine |
| dehydroimidazolones | | MGO-Arginine |

Pyrrolopyrridinium
Arginine - Lysine dimer (ALS)
Arginine Pyridinium
Cypentodine
Piperidinedinone enol
Vesperlysine
MRX

SUMMARY OF THE INVENTION

Five compounds have been found which are active in breaking AGE-protein cross-links. These compounds are L-bis-[4-(4-chlorobenzamidophenoxyisobutyryl)cystine] (LR20); 4-(3,5-dichlorophenylureido)phenoxyisobutyryl-1-amidocyclohexane-1-carboxylic acid (LR23); methylene bis [4,4'-(2-chlorophenylureidophenoxyisobutyric acid)] (LR90); 5-aminosalicylic acid (5-ASA); and metformin.

In one aspect of the invention, these AGE-breaking compounds are used to break glycation endproducts or cross-linked proteins in an organism by administering to an organism an effective amount of one or more of the AGE-breakers.

In a second aspect of the invention, the deleterious effects of aging in an organism are reversed by administering an effective amount of an AGE-breaker to the organism.

In a third aspect of the invention, complications resulting from diabetes in an organism are reversed by administration of an effective amount of an AGE-breaker to the organism.

In further aspects of the invention, the progress of disease in a patient, wherein the disease can include rheumatoid arthritis, Alzheimer's disease, uremia, neurotoxicity, or atherosclerosis, is reversed by administration of an effective amount of an AGE-breaker to the patient.

DETAILED DESCRIPTION OF THE INVENTION

Figure 1A:
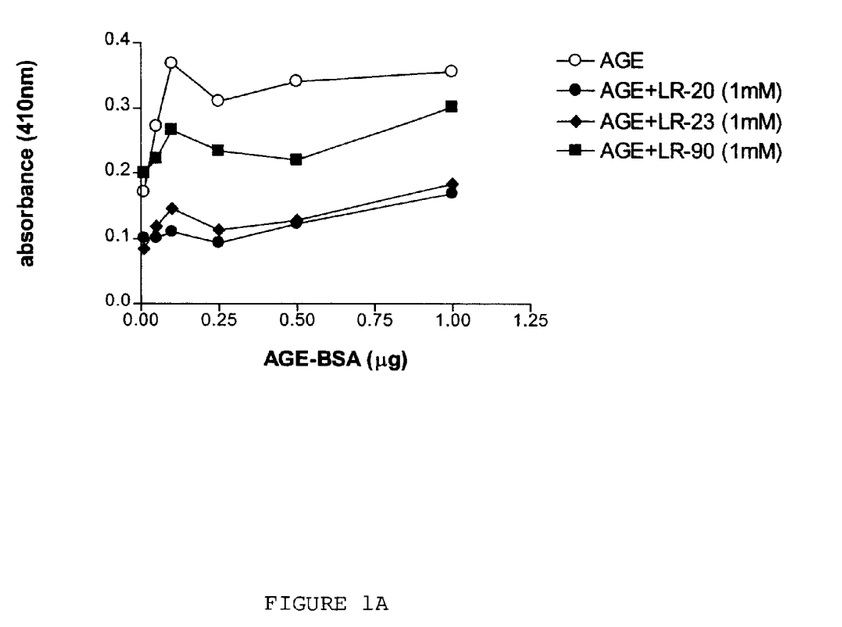
FIG. 1A shows the cleavage of cross-linked collagen-AGE-BSA by LR20, LR23 and LR90. AGE represents collagen-AGE-BSA in the absence of any AGE-breaker.
Figure 1B:
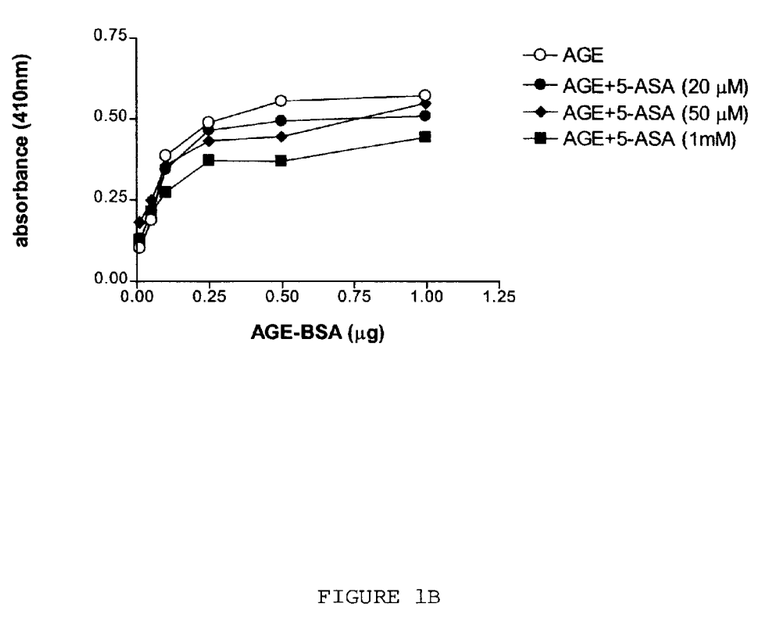
FIG. 1B shows the dose dependent AGE-breaking activity of 5-ASA by measuring cleavage of cross-linked collagen-AGE-BSA. AGE represents collagen-AGE-BSA in the absence of 5-ASA.

We have reported a new class of compounds, aryl (and heterocyclic) ureido and aryl (and heterocyclic) carboxamido phenoxyisobutyric acids, as inhibitors of glycation and AGE formation. A number of highly effective inhibitors were among the 92 compounds tested (Rahbar et al., 1999; Rahbar et al., 2000a). These were selected for in vivo experimentation in streptozotocin (STZ) induced diabetic rats. Recent reports on the discoveries of novel compounds, such as phenacylthiazolium bromide (PTB) (Vasan et al., 1996) and ALT 711 (Wolffenbuttel et al., 1998), which are able to cleave selectively the established AGE-protein cross-links in tissues and in in vitro induced AGE-cross-links, have been exciting. Furthermore, ALT 711 was reported to reverse the age-related increase of myocardial stiffness in vivo (Asif et al., 2000). Disclosed here are the results of an investigation of AGE-breaking properties of a large number of compounds we have recently developed as potent inhibitors of glycation and AGE-formation (Rahbar et al., 1999; Rahbar et al., 2000a). Using a specific ELISA technique and other in vitro assays for screening our compounds, five compounds have been found to be powerful AGE-cross-link breakers. These compounds are: L-bis-[4-(4-chlorobenzamidophenoxy isobutyryl) cystine (LR20); 4-(3,5-dichlorophenylureido)-phenoxyisobutyryl-1-amidocyclohexane-1-carboxylic acid (LR23); methylene bis [4,4'-(2-chlorophenylureidophenoxyisobutyric acid)] (LR90); 1,1-dimethylbiguanide (metformin); and 5-aminosalicylic acid (5-ASA). The structures of LR20, LR23 and LR90 are:

As described in the Examples below, compounds LR20, LR23 and LR90 in this study were each used at 1 mM final concentration and were very effective AGE-breakers as demonstrated in FIG. 1A. 5-ASA was used at 20 μM, 50 μM and 1 mM and demonstrated dose dependent AGE-breaking activities as shown in FIG. 1B. This characteristic of 5-ASA may be one of the reasons this drug is effective in the treatment of "ulceritis colitis" and Crohn disease. Furthermore, this drug may have beneficial effects in reversing AGE-cross-links in rheumatoid arthritis where accumulation of AGE in collagen and an immunological response to IgG damaged by glyoxidation (AGE-IgG) have been reported recently (Lucey et al., 2000). Finally, 5-ASA may have some effects on reducing damage of the β-amyloid contents of Alzheimer plaques.

Metformin, a highly popular drug for the treatment of Type 2 diabetes, was found by us to be a potent inhibitor of glycation (Rahbar et al., 2000b). In the Examples below evidence is presented that metformin is also a moderate AGE-breaker.

The mechanism of action of our AGE-breaker compounds is yet to be discovered. However, since these compounds release BSA from the preformed AGE-BSA-Collagen complex as detected immunochemically by ELISA, we assume these AGE-breakers are able to chemically cleave α-diketones by breaking the chemical bond between the carbonyl groups, similar to the PTB mechanism of action (Ulrich and Zhang, 1997).

The present invention is further detailed in the following Examples, which are offered by way of illustration and are not intended to limit the invention in any manner. Standard techniques well known in the art or the techniques specifically described below are utilized.

EXAMPLE 1

Compounds and Materials

LR20, LR23 and LR90 were synthesized in our laboratory. These compounds are easily synthesized by those of skill in the art. These are among the 92 compounds we have developed as inhibitors of glycation and AGE formation (Rahbar et al., 1999). Metformin (1,1-dimethylbiguanide) and 5-aminosalicylic acid (5-ASA) were purchased from Sigma.

Rat tail-tendon-collagen coated 96 well plates were purchased from Biocoat (Collaborative Research, Bedford, Mass.) and used according to the manufacturer's instructions. Rabbit polyclonal anti-BSA antibody, a horseradish peroxidase-linked goat anti-rabbit antibody, and rat-tail-collagen (type VII, acid soluble) were purchased from Sigma and $H_2O_2$ substrate containing ABTs (2,2'-azino-di-3-ethylbenzthiazoline sulfonic acid) as chromogen was purchased from Zymed. BSA, glucose, human IgG, rabbit-anti-rat and anti-human IgGs and methylglyoxal were from Sigma. Amicon filters (cut-off 10,000 Da) were obtained from Amicon (Beverly, Mass.). Spectra/Por CE dialysis membrane (molecular cut-off 1000 Da) was from Spectrum Inc. Thioflavin-T (ThT) and Congo Red (CR) were from Sigma.

EXAMPLE 2

Evaluation of Cleavage of Glycated BSA by AGE-breaker Compounds

In vitro evaluation of the ability of the AGE-breaker compounds to cleave and break cross-linking of glycated BSA (AGE-BSA) (prepared as described (Rahbar et al., 1999)) to the rat-tail-tendon-collagen was by a special ELISA (Al-Abed et al., 1999). The rat-tail-tendon-collagen coated plate was blocked first with 300 μL of Superbloc blocking buffer for one hour. The blocking solution was removed from the wells by washing the plate twice with PAS-Tween 20 using a Dynatech ELISA-plate washer. Cross-linking of AGE-BSA (0.25, 0.50, 0.75, 1 and 1.25 μg per well) to rat-tail-collagen coated plates was performed without the testing compound and incubated for 5 hours at 37° C., after which the wells were washed with PBS/0.05% Tween to remove the unattached AGE-BSA. Test concentrations of the compound (50 μL) dissolved in PBS were added to wells in triplicate and incubation continued at 37° C. overnight followed by three times washing the wells with PBS/Tween. The amount of BSA remaining attached to the tail collagen plate was then quantified by the rabbit polyclonal anti-BSA antibody, a horseradish peroxidase conjugated secondary antibody, goat anti-rabbit immunoglobulin and incubation for 30 minutes. The substrate (ABTs chromogen, Zymed) was added and read at $A_{410}$ in an ELISA plate reader (BioRad).

The percentage breaking activity is calculated by the following formula:

$$1000 \times [(A_{410}, \text{PBS control}) - (A_{410}, \text{AGE-breaker compound})] / [A_{410}, \text{PBS control}].$$

EXAMPLE 3

In Vitro Cross-linked Complex Formation Assay

AGE-BSA (2 mg/ml in PBS containing 0.02% $NaN_3$ and 1 mM EDTA) and rat-tail-collagen (2 mg/mL in 1% acetic acid) were mixed in a ratio of 1:4 (v/v) and incubated for 24 hours in aseptic conditions at 37° C. and constant shaking. At the end of the incubation period, the mixture was distributed and aliquots of 200 μL were prepared in microfuge tubes and the AGE-Breaker compound was added to the test sample at a final concentration of 1 millimole/L, with the control tubes receiving PBS only. Test and control tubes were incubated at 37° C. with mild shaking for 24 hours. 25 μg of each reaction was added to Laemmli preparation buffer and heated at >90° C. for 10 minutes and loaded into 6% gels (reducing SDS-PAGE (6 percent, Tris glycine gels)). Electrophoresis was carried out for 1 hour at 10 μA and then 20 μA until dye front was off the gel. The gel was stained with Amido Black and destained with methanol-acetic acid-water. Gels were dried and photographed.

EXAMPLE 4

Cleavage of AGE Cross-links that Form in Vivo

AGE-breaker treatment in vitro can also decrease AGE cross-links that form in situ in diabetic, rat-tail-tendon collagen. For this study, diabetes is first induced in male Lewis rats (150–175 g) by the injection of streptozotocin (65 mg/kg, i.p.). Hyperglycemia is then confirmed 1 week later by plasma glucose measurement ($\geq 250$ mg/dL). Thirty-two weeks later, the rats are sacrificed and collagen is isolated from the tail tendon fibers by a standard protocol (Vasan et al., 1996). The insoluble collagen is treated with cyanogen bromide (Vasan et al., 1996) and the hydroxyproline content is measured (Vasan et al., 1996). Aliquots containing 1 μg equivalent of hydroxyproline are subjected to SDS-PAGE under reducing conditions and are stained with Coomassie blue. Because diabetic collagen contains nonreducible AGE cross-links, cyanogen bromide cleavage results in a pattern of higher molecular weight fragments than that observed in collagen obtained from non-diabetic animals. AGE-breaker treatment of diabetic collagen restores the electrophoretic pattern to that observed with non-diabetic collagen.

EXAMPLE 5

Determination of Cleavage of IgG-AGE Cross-linked to the Rat RBC Surface Using an Anti-IgG ELISA Assay IgG-cross-linked to the RBC surface is determined in an anti-IgG ELISA adapted for use with cellulose-ester-membrane-sealed 96 well microtiter plates (Multiscreen-HA, Millipore) (Vasan et al., 1996). Heparinized blood is washed three times with PBS; the packed RBC are diluted 1:250–1:500 in PBS. Membrane-containing wells are first blocked with 0.3 mL Superbloc (Pierce), then washed with 0.3 mL PBS/0.05% Tween, followed by 0.1 mL PBS. RBCs are gently vortexed and 50 μL aliquots pipetted into wells. Cells are then washed and 50 μL of a polyclonal rabbit anti-rat IgG (Sigma, diluted 1:25,000) is added. After incubation at room temperature for 2 hours, the cells are washed 3 times with PBS, once with Tris-buffered saline, and 0.1 mL p-nitrophenyl phosphate substrate is added (1 mg/mL in 0.1 M diethanolamine buffer, pH 9.5). The ability of AGE-breaker compound to reduce RBC-surface IgG in vitro is evaluated as follows.

RBCs from diabetic rats are washed and 0.1 mL aliquots are incubated overnight at 37° C. with 1 mL AGE-breaker compound in PBS. Control incubations contain RBCs and PBS alone. At the end of the reaction, RBCs are assayed for RBC-IgG; per cent decrease is calculated as $100 \times ((A_{410}, \text{PBS control}) - (A_{410}, \text{AGE-breaker compound}))/(A_{410}, \text{PBS control})$. Diabetic rats are treated for up to 4 weeks with AGE-breaker compound (10 mg/kg q.d. by oral gavage) or saline as control (n=4–6 rats per group). At intervals, blood is collected from tail veins into heparinized tubes, washed 3 times with 10 volumes of PBS, and assayed for surface IgG.

EXAMPLE 6

Disaggregation of β-Amyloid Fibrils in Vitro

AGE-modified β-amyloid peptide, prepared by the incubation of glucose with β-AP (amino acids 1–40, from Bachem, Torrance, Calif.), has been shown to initiate efficiently the aggregation and polymerization of β-AP into amyloid fibrils in vitro.

Originally this assay was used for PTB (Al-Abed et al., 1996) and showed that PTB at 20 mM concentration disaggregates β-amyloid fibrils that have been aggregated in this manner. In the original version of this assay, AGE-β-amyloid had to be radioiodinated and then dialyzed to remove the unincorporated radioiodine $^{125}$I and separated by SDS-PAGE in a 4–10% gradient gel which makes this assay very cumbersome.

In a new version of this assay, Bucala and Callaway (Bucala, personal communication; Tjemberg et al., 1999) have proposed the following approaches to demonstrate the disaggregation of the AGE-p-amyloid peptide by the AGE-breaker compounds. The Thioflavin T (ThT) fluorescence assay and Congo Red binding assay are based on the fact that Congo Red and ThT undergo characteristic spectral alteration on binding to a variety of amyloid fibrils that do not occur on binding to the precursor polypeptides and monomers. Both dyes are adapted to in vitro measurements of amyloid fibril formation and quantification. ThT binding to β-amyloids gives rise to a large fluorescence excitation spectral shift that allows selective excitation of the amyloid fibril bound ThT (Tjernberg et al., 1999).

EXAMPLE 7

Preparation of an AGE Glycation β-amyloid (Al-Abed et al., 1999)

β-amyloid (836 μg) is dissolved in 0.1 mL double-distilled water and 0.1 mL of 0.4 M sodium phosphate buffer (pH 7.4) containing 1 M D-(+)-glucose and then 2 mM EDTA is added. This is followed by the addition of 1.1 mL of 0.2 M sodium phosphate buffer (pH 7.4) containing 1 M D-(+)-glucose and 1 mM EDTA. The final concentrations of p-AP and glucose are 178.4 µM and 1 M, respectively. The resulting gelatinous solution is incubated for 3 months at 37° C. in the dark and then dialyzed against double-distilled water using a Spectra/Por CE dialysis membrane (molecular mass cut off: 1000 Da, Spectrum Inc., Houston, Tex.). Control preparations are incubated under the same conditions, but in the absence of D-(+)-glucose.

EXAMPLE 8

Treatment of AGE-β-amyloid with the AGE-breaker Compound (Asif et al., 2000)

AGE-β-AP prepared as above is dissolved at 200 µM in 50 mM Tris-buffered saline (TBS), (450 mM NaCl), pH 7.4 and incubated alone or with 1 mM of the AGE-breaker compound for 24 hours at 37° C. In control experiments, the peptide is initially dissolved in 2 volumes of 50 mM Tris, pH 10, to ensure starting solutions free from possible fibril seeds. After 3 minutes, 1 volume of 50 mM Tris-HCl containing 450 mM NaCl is added to give a final pH of 7.4 and a concentration of 150 mM NaCl.

EXAMPLE 9

Thioflavine T (ThT) Fluorescence Assay (Tiemberg et al., 1999)

The incubated samples are vortexed and 40 µL aliquots are withdrawn and mixed with 960 µL of 10 µM ThT in 10 mM phosphate-buffered saline and examined on a fluorescence spectrophotometer with excitation of 437 nm and emission at 485 nm. Slit widths are set to 5 nm.

EXAMPLE 10

Quantifying β-amyloid Aggregation and Disaggregation

Using the Congo Red Spectrophotometric Assay (Klunk et al., 1999)

Congo red (CR) is a histologic dye that binds to many amyloid proteins because of their extensive β-sheet structure. The absorbance spectrum of the dye changes upon binding to amyloid. This spectral change has previously been exploited to develop a method to study the interaction of CR with fibrillar β-sheet insulin fibrils, a model amyloid protein.

To perform an assessment of amyloid β (Aβ) aggregation by the CR-β-amyloid method, one needs to measure the absorbance of the amyloid test samples at two wavelengths (403 and 541 nm). This, along with separate measurements of CR and β-amyloid alone at the same wavelengths, provides the data necessary to complete the appropriate calculations and affords an accurate and absolute quantification of the concentration of aggregated β-amyloid in the test sample.

EXAMPLE 11

Congo Red Preparation

A 100–300 µM stock solution of Congo red is prepared in filtered phosphate-buffered saline (PBS, Sigma; 0.01 M phosphate buffer, 0.0027 M KCl, and 0.137 M NaCl, pH 7.4) and 10% ethanol. Ethanol is added to the stock solution to prevent CR micelle (micro-aggregate) formation. This CR stock solution is filtered three times using Gelman extra-thick glass fiber filters (~0.3 µm nominal pore retention). The concentration of the stock solution is determined by measuring the absorbance of an aliquot of the filtrate at 505 nm. A molar absorbance value for CR in 40% ethanol (in 1 mM $NaH_2PO_4$, pH 7.0) of $5.93 \times 10^4$ AU/(cm M) at 505 nm is determined after quantifying the concentration of a CR solution in deuterium-6-dimethyl sulfoxide with an internal standard by proton NMR.

EXAMPLE 12

Congo Red Binding Assays (Klunk et al. 1999)

CR-β-amyloid binding studies are conducted using spectrophotometric analysis on a Beckman DU 640 spectrophotometer; all measurements are taken in wavelength-scanning mode (300–700 nm), and the instrument is blanked on PBS unless otherwise indicated. Binding experiments are performed in three sets. In the first, varying concentrations of CR (0.6–6.1 µM) are incubated with 97.2 µg/mL of Aβ fibrils, an amount shown to bind >97% of the highest concentration of CR by filtration assays. Mixtures of CR and β-amyloid fibrils are incubated at room temperature for 15 minutes prior to spectral analysis. Absorbance spectra from 300 to 700 nm are recorded for the CR-β-amyloid mixture treated first with the AGE-breaker compound as well as CR and β-amyloid alone at the appropriate concentrations.

EXAMPLE 13

Electron Microscopy (Kapurniotu et al., 1998)

The incubated samples of control and fibrillar AGE-β-amyloid peptide (AGE-β-AP) (see Example 8) are centrifuged at 20,000×g for 20 minutes and then supernatants are aspirated. The pellets are sonicated for 5 seconds in 100 µL double distilled $H_2O$ and 8 µL of these suspensions are placed on grids covered by a carbon-stabilized Formvar-coated copper grid. Excess fluids are withdrawn after 30 seconds and the grids are negatively stained with 3% uranyl acetate in water. The stained grids are then examined and photographed in a JEOL 100 cx at 60 KV.

EXAMPLE 14

ELISA Assay to Screen AGE-cross-link Breaker Compounds

We tested the ability of our compounds to disrupt the cross-links that form when AGE-BSA is allowed to react with unglycated native rat collagen and to release BSA from preformed AGE-BSA-collagen complex. The specific ELISA assay, which is based on that principle, was used to screen more than 100 compounds available to us for possible AGE-cross-link breaking activity. Among those, five compounds revealed such an AGE-cross-link cleaving activity. FIG. 1A shows examples of the results obtained with the ELISA assay on LR20, LR23 and LR90 and FIG. 1B demonstrates the ability of three different concentrations of 5-ASA on breaking cross-linked AGE-BSA-collagen complex.

EXAMPLE 15

Cleavage of AGE-cross-links Formed in Vivo

The ability of the five compounds to cleave cross-links formed in vivo by glycated immunoglobulin G (IgG-AGE)

and red cell membrane of diabetic rats is tested as follows. Red cells are isolated from normal and diabetic rats and the amounts of surface-bound IgG before and after treatment in vitro with each compound are measured. Considerably higher amounts of IgG are bound to the cell surface of diabetic red cells compared with non-diabetic red cells. The amount of membrane-bound IgG will be lower in the red cells treated with the AGE-breakers as compared to untreated diabetic red cells.

EXAMPLE 16

Cleavage of the in Vitro Formed AGE-BSA-Collagen Complex in Test Tubes

Figure 2:
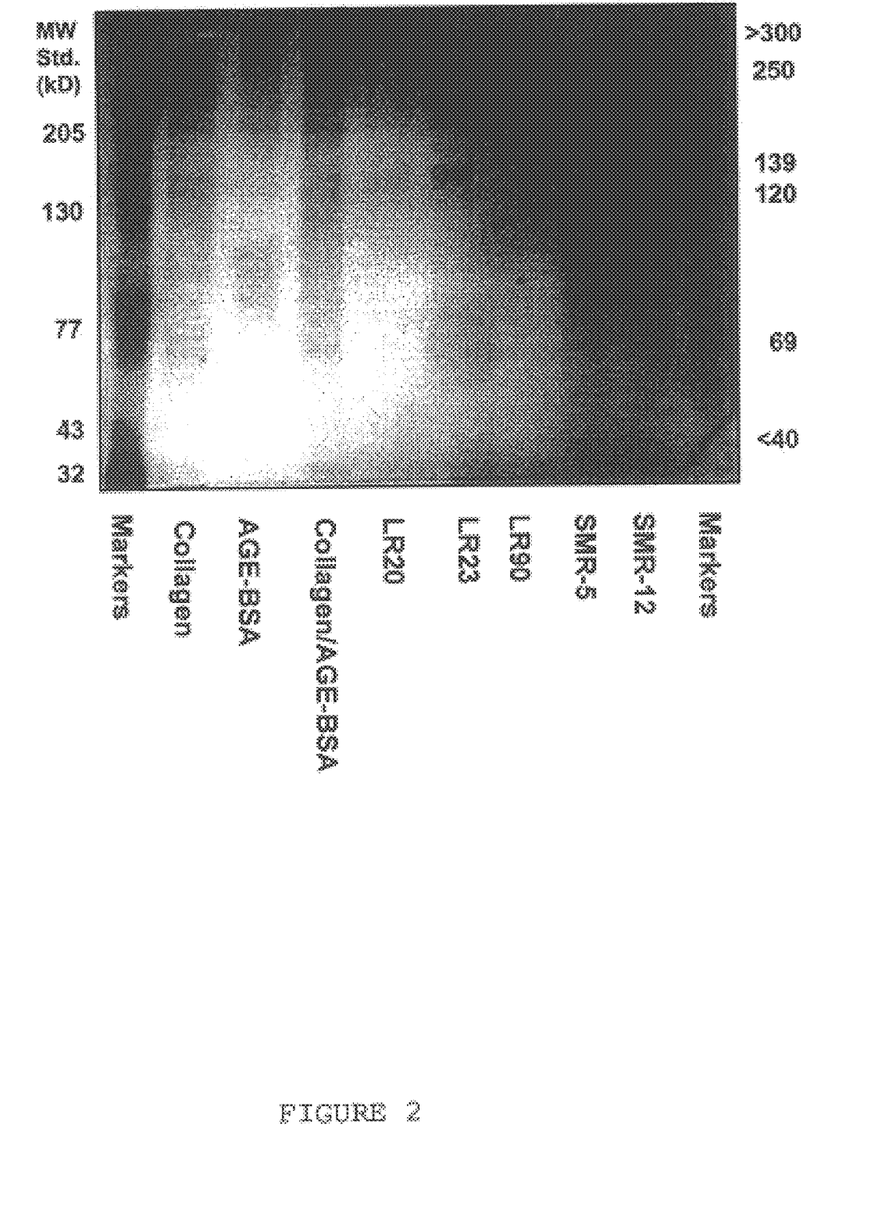
FIG. 2 shows an Amido Black stained gel demonstrating the breaking by AGE-breaker compounds of cross-linked collagen-AGE-BSA. Lanes 1 and 10 are molecular weight markers. Lane 2 is collagen, lane 3 is cross-linked AGE-BSA, and lane 4 is cross-linked collagen-AGE-BSA. Lanes 5–9 are cross-linked collagen-AGE-BSA which has been treated with LR20, LR23, LR90, 5-ASA and metformin, respectively.

AGE-BSA cross-linked to the rat-tail-collagen in test tubes was treated with AGE-breaker compound followed by SDS-PAGE. FIG. 2 demonstrates such an electrophoretic separation. The high molecular weight band near the origin is assumed to represent the AGE-BSA-collagen complex. Lanes 5–9 (LR20, LR23, LR90, 5-ASA (shown as SMR-5) and metformin (shown as SMR-12)) demonstrate AGE-breaking activities. This is seen by the decreased amount of material seen at >300 kDa and the decrease in the amount of material in the 139 kDa band. These changes are dramatic for LR20 and LR90 and are seen, though less dramatically, for LR23, 5-ASA and metformin. Lanes 1 and 10 are molecular weight markers and lanes 2–4 are controls as described in the legends.

EXAMPLE 17

Cleavage of the in Vivo Formed AGE-Collagen in STZ Induced Diabetic Rats

Collagen isolated from tail-tendon fibers of diabetic Lewis rats is prepared and treated with an AGE-breaker. The insoluble collagen is then treated with cyanogen bromide. Aliquots from normal and diabetic rat collagens are run on SDS-PAGE under reducing conditions and stained. Treatment of collagen with AGE breakers will show solubilization of the insoluble AGE-collagen.

EXAMPLE 18

Assay Tests Based on Disaggregation of β-amyloid Fibrils in Vitro

AGE-breakers are able to disaggregate β-amyloid fibrils formed in vitro. Disaggregation of AGE-β-amyloid is detected and measured in 3 different assays.

1) ThT Fluorescence Assay

There are shifts in excitation and emission maxima upon binding ThT to amyloid fibrils and this has been used to monitor amyloid fibril formation (Tjernberg et al., 1999) and disaggregation. Both soluble and fibrillar β-amyloid are analyzed for ThT binding in a fluorescence assay. Free ThT fluoresces weakly at 438 nm when excited at 350 nm. In the presence of amyloid fibrils, a strong ThT fluorescence emission is observed at 490 nm upon excitation at 450 nm. The emission is linear relative to the concentration of fibrils. The excitation emission spectra obtained from β-amyloids treated and untreated with AGE-breaker display a shift from the free dye.

2) Congo Red Binding Assay

Congo Red binding assays as described in Example 12 are performed and demonstrate the quantification of the AGE-β-amyloid disaggregation by AGE-breakers.

3) Electron Microscopy

Electron microscopic examination of the preparations of AGE-breaker treated and untreated β-amyloid fibrils reveals differences in the fibrillar form of the β-amyloid aggregates before and after treatment with the AGE-breaker. In control (untreated) preparations, β-amyloid shows dense fibrillar aggregates, whereas preparations of β-amyloid treated with an AGE-breaker show fibrils which are less dense and non-uniform. This result suggests that the AGE-breaker compound has the ability to disaggregate the β-amyloid fibrillar structure.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Al-Abed, Y., Liebich, H., Voelter, W., and Bucala, R. Hydroxyalkenal formation induced by advanced glycosylation of low density lipoprotein. *J Biol. Chem* 271:2892–2896, 1996.

Al-Abed, Y., Kapurniotu, A., Bucala, R., Advanced glycation end products: Detection and reversal. *Methods in Enzymology*, 309:152–172, 1999.

Asif, M., Egan, J., Vasan, S., Jyothirmayi, G. N., Masurekar, M. R., Lopez, S., Williams, C., Torres, R. L., Wagle, D., Ulrich, P., Cerami, A., Brines, M., and Regan, T. J. An advanced glycation endproduct cross-link breaker can reverse age-related increases in myocardial stiffness. *Proc. Natl. Acad Sci., USA* 97:2809–2813, 2000.

Bailey, A. J., Paul, R. G., and Knott, L. Mechanisms of maturation and ageing of collagen. Mechanisms of Ageing and Development, 106:1–56, 1998.

Baynes, J. W., and Thorpe, S. R. Perspective in diabetes: role of oxidative stress in diabetic complications: A new perspective on an old paradigm. *Diabetes* 48:1–9, 1999.

Beisswenger, P., Smith, K., Howell, S., Touchette, A., and Szwergold, B. Accelerated diabetic nephropathy is associated with increased methylglyoxal production. Am. Diab. Assoc., 58$^{th}$ Annual Meeting, #312, Chicago, June 1998.

Boel, E., Selmer, J., Flodgaard, H. J., Jensen, T., Diabetic late complications: will aldose reductase inhibitors or inhibitors of advanced glycosylation endproduct formation hold promise? *J Diab. Compl.* 9:104–129, 1995.

Brownlee, M. Lilly Lecture 1993. Glycation and diabetic complications. Diabetes, 43:836–841, 1994.

Bucala, R. Lipid and lipoprotein modification by advanced glycosylation end-products: Role in atherosclerosis. *Experimental Physiology*, 82:327–337, 1997.

Bucala, R. and Cerami, A. Advanced glycosylation: chemistry, biology and implications for diabetes and aging. *Adv. Pharmacol* 23:1–34, 1992.

Bucala, R. and Rahbar, S. Protein glycation and vascular disease in Endocrinology of cardiovascular function. Edited by E. R. Levin and J. L. Nadler, Kluwer Acad. Publishers, p 159–180, 1998.

Bucala, R., Model, P., Cerami, A. Modification of DNA by reducing sugars: a possible mechanism for nucleic acid aging and age-related dysfunction in gene expression. *Proc. Natl. Acad Sci. U.S.A.*, 81:105–109, 1984.

Bucala, R. Makita, Z., Koschinsky, T., Cerami, A., Vlassara, H. Lipid advanced glycosylation: pathway for lipid oxidation in vivo. *Proc. Natl. Acad Sci. USA* 90:6434–6438, 1993.

Bucala, R., Makita, Z., Vega, G., Grundy, S., Koschinsky, T., Cerami, A. and Vlassara, H. Modification of low density lipoprotein by advanced glycation end products contributes to dyslipidemia of diabetes and renal insufficiency. *Proc. Natl. Acad. Sci. U.S.A.*, 91:9441–9445, 1994.

The Diabetes Control and Complications Trial Research Group: The effect of intensive treatment of diabetes on the development and progression of long-term complications in insulin-dependent diabetes mellitus. *N Engl J Med* 329:977–986, 1993.

Gilcrease, M. Z., and Hoover, R. L. Human monocyte interactions with non-enzymatically glycated collagen. *Diabetologia*, 35:160–164, 1992.

He, C., Sabol, J., Mitsuhashi, T., and Vlassara, H. Dietary glycotoxins: Inhibition of reactive products by aminoguanidine facilitates renal clearance and reduces tissue sequestration. *Diabetes*, 48:1308–1315, 1999.

Hedrick CC, Thorpe SR, Fu MX, Harper CM, Yoo J, Kim SM, Wong H, Peters AL. Glycation impairs high-density lipoprotein function. *Diabetologia* 43:312–320, 2000.

Horie, K., Miyata, T., Maeda, K., Miyata, S. Sugiyama, S., Sakai, H., Strihou, C., Monnier, V. M., Witztum, J. L., and Kurokawa, K. Immunohistochemical colocalization of glycoxidation products and lipid peroxidation products in diabetic renal glomerular lesions. Implication for glycoxidative stress in the pathogenesis of diabetic nephropathy. *J Clin. Invest.* 100:2995–3004, 1997.

Iijima, K., Murata, M., Takahara, H., Irie, S., and Fujimoto, D. Identification of $N^\omega$-carboxymethylarginine as a novel acid-labile advanced glycation end product in collagen. *Biochem. J.*, 347Ptl :23–27, 2000.

Kapurniotu, A., Bernhagen, J., Greenfield, N., Al-Abed, Y., Teichberg, S., Frank, R. W., Voelter, W., and Bucala, R. Contribution of advanced glycosylation to the amyloidogenicity of islet amyloid polypeptide. *Eur. J Biochem.*, 251:208–216, 1998.

Khalifah, R. G., Baynes, J. W., and Hudson, B. G. Amadorins: Novel post-amadori inhibitors of advanced glycation reactions. *Biochem. Biophys. Res. Commun.* 257:251–258, 1999.

Klunk, W. E., Jacob, R. F., and Mason, R. P. Quantifying amyloid β-peptide (Aβ) aggregation using the Congo Red-Aβ (CR-Aβ) spectrophotometric assay. *Analytical Biochemistry*, 266:66–76, 1999.

Kochakian, M., Manjula, B. N., and Egan, J. J. Chronic dosing with aminoguanidine and novel advanced glycosylation end product-formation inhibitors ameliorates cross-linking of tail tendon collagen in STZ-induced diabetic rats. *Diabetes* 45:1694–1700, 1996.

Koschinsky, T., He, C. J., Mitsuhashi, T., Bucala, R., Liu, C. Buenting, C., Heitmann, K. and Vlassara, H. Orally absorbed reactive glycation products (glycotoxins): An environmental risk factor in diabetic nephropathy. *Proc Natl. Acad. Sci. U.S.A.* 94:6474–6479, 1997.

Lapolla, A., Fedele, D., Garbeglio, M., Martano, L., Tonani, R., Seraglia, R., Favretto, D., Fedrigo, M.A., and Traldi, P. Matrix-assisted laser desorption/ionization mass spectrometry, enzymatic digestion, and molecular modeling in the study of nonenzymatic glycation of IgG. *J. Am. Soc. Mass. Spectrom*, 11:153–159, 2000.

Lucey, M. D., Newkirk, M. M., Neville, C., Lepage, K., and Fortin, P. R. Association between IgM response to IgG damaged by glyoxidation and disease activity in rheumatoid arthritis. *J. Rheumatol.* 27:319–323, 2000.

Makita, Z., Radoff, S., Rayfield, E. J., Yang, Z. H., Skolnik, E., Delaney, V., Friedman, E. A., Cerami, A. and Vlassara, H.N. Advanced glycosylation end products in patients with diabetic nephropathy. *N. Eng. J Med.* 325:836–842, 1991.

Makita, Z., Bucala, R., Rayfield, E. J., Friedman, E. A., Kaufman, A. M., Korbet, S. M., Barth, R. H., Winston, J. A., Fuh, H., Manogue, K. R., Cerami, A. and Vlassara, H. Reactive glycosylation endproducts in diabetic uraemia and treatment of renal failure. *Lancet*, 343:1519–1522, 1994.

Matsumoto, K., Ikeda, K., Horiuchi, S., Zhao, H., and Abraham, E. C. Immunochemical evidence for increased formation of advanced glycation end products and inhibition by aminoguanidine in diabetic rat lenses. *Biochem. Biophys. Res. Commun.*, 241, 352–354, 1997.

McLellan, A. C., Thornalley, P. J., Benn, J. and Sonksen, P. H. Glyoxalase system in clinical diabetes mellitus and correlation with diabetic complications. *Clin. Sci. (Colch)*, 87:21–29, 1994.

Onorato, J. M., Thorpe, S. R., and Baynes, J. W. Immunohistochemical and ELISA assays for biomarkers of oxidative stress in aging and disease. *Ann, N.Y. Acad. Sci.* 854:277–290, 1998.

Park, L., Raman, K. G., Lee, K. J., Lu, Y., Ferran, L. J., Chow, W. S., Stem, D., and Schmidt, A. M., Suppression of accelerated diabetic atherosclerosis by the soluble receptor for advanced glycation endproducts. *Nature Med.* 4:1025–1031, 1998.

Phillips, S. A., and Thornalley, P. J. The formation of methylglyoxal from triose phosphates. Investigation using a specific assay for methylglyoxal. *Eur. J Biochem.* 212:101–105, 1993.

Rahbar, S., Kumar Yernini, K., Scott, S., Gonzales, N., and Lalezari, I. Novel inhibitors of advanced glycation endproducts. *Biochem. Biophys. Res. Commun.*, 262:651–656, 1999.

Rahbar, S., Yemeni, K., Scott, S., Gonzales, N., and Lalezari, I. Novel inhibitors of advanced glycation endproducts (PART II), *Biochem. Biophys. Res. Commun.* (2000a) submitted.

Rahbar, S., Natarajan, R., Yerneni, K., Scott, S., Gonzales, N. and Nadler, J. L., Evidence that pioglitazone, metformin and pentoxyfylline are inhibitors of glycation. *Clin. Chimica. Acta* (2000b) (in press).

Requena, J. R., Ahmed, M. U., Fountain, C. W., Degenhardt, T. P., Reddy, S. R., Perez, C., Lyons, T. J., Jenkins, A. J., Baynes, J. W., Thorpe, S. R. Carboxymethylethanolamine, a biomarker of phospholipid modification during the Maillard reaction IN VIVO. *J. Biol. Chem.* 272:17473–17479, 1997.

Schalkwijk, C. G., Vermeer, M. A., Stehouwer, C. D. A., te Koppele J., Princen, H. M. G., Van Hinsbergh, V. W. M. Effect of methylglyoxal on the physico-chemical and biological properties of low-density lipoprotein. *Biochim. Biophys. Acta* 1394:187–198, 1998.

Schmidt, A. M., Hasu, M., Popov, D., Zhang, J. H., Chen, J., Yan, S. D., Brett, J., Cao, R., Kuwabara, K., Costache, J., Simionescu, N. and Stem, D. Receptor for advanced glycation end products (AGEs) has a central role in vessel wall interactions and gene activation in response to circulating AGE protein. *Proc. Natl. Acad Sci, USA*, 91:8807–8811, 1994.

Silbiger, S., Crowley, S., Shan, Z., Brownlee, M., Satriano, J., Schlondorff, D. Nonenzymatic glycation of mesangial matrix and prolonged exposure of mesangial matrix to elevated glucose reduces collagen synthesis and proteoglycan charge. *Kidney Int.* 43:853–864, 1993.

Slatter, D., Bolton, C. H., and Bailey, A. J. The importance of lipid-derived malondialdehyde in diabetes mellitus. *Diabetologia*, 43:550–557, 2000.

Soulis-Liparota, T., Cooper, M., Papazoglou, D., Clarke, B. and Jerums, G. Retardation by arninoguanidine of development of albuminuria, mesangial expansion, and tissue fluorescence in streptozocin-induced diabetic rat. *Diabetes*, 40:1328–1334, 1991.

Takahashi, M., Pischetsrieder, M., Monnier, V. M. Isolation, purification, and characterization of amadoriase isoenzymes (fructosyl amine-oxygen oxidoreductase EC 1.5.3) from Aspergillus sp. *J Biol Chem*, 272:3437–3443, 1997.

Thornalley, P. J., and Minhas, H. S. Rapid hydrolysis and slow alpha,beta-dicarbonyl cleavage of an agent proposed to cleave glucose-derived protein cross-links. *Biochem. Pharmacol.* 57:303–307, 1999.

Tjemberg, L. O., Callaway, D. J. E., Tjemberg, A., Hahne, S., Lilliehook, C., Terenius, L., Thyberg, J., and Nordstedt, C. A molecular model of Alzheimer amyloid β-peptide fibril formation. *J Biol. Chem.*, 274:12619–12625, 1999.

Ulrich, P., and Zhang, X. Pharmacological reversal of advanced glycation end-product-mediated protein crosslinking. *Diabetologia*, 40: S157-S159, 1997.

Vasan, S., Zhang, X., Zhang, X. I., Kapumiotu, A., Bernhagen, J., Teichberg, S., Basgen, J., Wagle, D., Shih, D., Terlecky, I., Bucala, R., Cerami, A., Egan, J., and Ulrich, P. An agent cleaving glucose-derived protein crosslinks in vitro and in vivo. *Nature*, 382:275–278, 1996.

Vlassara, H., Fuh, H., Donnelly, T., and Cybulsky, M. Advanced glycation endproducts promote adhesion molecule (VCAM-1, ICAM-1) expression and atheroma formation in normal rabbits. *Mol Medicine* 1:447–456, 1995.

Westwood, M. E., Argirov, O. K., Abordo, E. A., and Thornalley, P. J. Methylglyoxal-modified arginine residues—a signal for receptor-mediated endocytosis and degradation of proteins by monocytic THP-1 cells. *Biochim. Biophys. Acta* 1356:84–94, 1997.

Wolffenbuttel, B. H. R., Boulanger, C. M., Crijns, F. R. L., Huijberts, M. S. P., Poitevin, P., Swennen, G. N. M., Vasan, S., Egan, J. J., Ulrich, P., Cerami, A., and Levy, B. I. Breakers of advanced glycation end products restore large artery properties in experimental diabetes. *Proc. Natl. Acad Sci., USA*, 95:4630–4634, 1998.

Yan, H. and Harding, J. J. Inactivation and loss of antigenicity of esterase by sugars and a steroid. *Biochim. Biophys. Acta*, 1454:183–190, 1999.

Yan, S. D., Stem, D., and Schmidt, A.M. What's the RAGE? The receptor for advanced glycation end products (RAGE) and the dark side of glucose. *Eur. J Clin. Invest.*, 27:179–181, 1997.

Yang, S., Thorpe, S. R., and Baynes, J. W. AGE-breakers fail to break cross-links in skin collagen of diabetic rats. *Diabetes*, 49 (Suppl. 1), A130, 2000.

Yim, H. S., Kang, S. O., Hah, Y. C., Chock, P. B., and Yim, M. B. Free radicals generated during the glycation reaction of arnino acids by methylglyoxal. A model study of protein-cross-linked free radicals. *J Biol. Chem.* 270:28228–28233, 1995.

What is claimed is:

1. A method of cleaving glycation endproducts or crosslinked proteins in an organism in need thereof, wherein said method comprises administering an effective amount of a compound or pharmaceutically acceptable salt thereof to said organism wherein said compound is selected from the group consisting of:

(a) L-bis-[4-(4-chlorobenzamidophenoxyisobutyryl) cystine];

(b) 4-(3,5-dichlorophenylureido)phenoxyisobutyryl-1-amidocyclohexane-1-carboxylic acid;

(c) methylene bis [4,4'-(2-chlorophenylureidophenoxyisobutyric acid)];

(d) 1,1-dimethylbiguanide; and (e) 5-aminosalicylic acid.

2. A method of reducing deleterious effects of aging by cleaving formed glycation endproducts or crosslinked proteins in an organism in need thereof, wherein said method comprises administering an effective amount of a compound or a pharmaceutically acceptable salt thereof to the organism wherein said compound is selected from the group consisting of:

(a) L-bis-[4-(4-chlorobenzamidophenoxyisobutyryl) cysteine];

(b) 4-(3,5-dichlorophenylureido)phenoxyisobutyryl-1-amidocyclohexane-1-carboxylic acid;

(c) methylene bis [4,4'-(2-chlorophenylureidophenoxyisobutyric acid)];

(d) 1,1-dimethylbiguanide; and (e) 5-aminosalicylic acid.

3. A method of reducing diabetic complications by cleaving formed glycation endproducts or crosslinked proteins in an organism in need thereof, wherein said method comprises administering an effective amount of a compound or a pharmaceutically acceptable salt thereof to the organism in need thereof, wherein said compound is selected from the group consisting of:

(a) L-bis-[4-(4-chlorobenzamidophenoxyisobutyryl) cysteine];

(b) 4-(3,5-dichlorophenylureido)phenoxyisobutyryl-1-amidocyclohexane-1-carboxylic acid;

(c) methylene bis [4,4'-(2-chlorophenylureidophenoxyisobutyric acid)];

(d) 1,1-dimethylbiguanide; and (e) 5-aminosalicylic acid.

4. A method of reducing progress of rheumatoid arthritis, Alzheimer's disease, uremia, neurotoxicity, or artherosclerosis in a patient by cleaving formed glycation endproducts or protein crosslinking, wherein said method comprises administering an effective amount of a compound or a pharmaceutically acceptable salt thereof to the organism in need thereof, wherein said compound is selected from the group consisting of:

(a) L-bis-[4-(4-chlorobenzamidophenoxyisobutyryl) cysteine];

(b) 4-(3,5-dichlorophenylureido)phenoxyisobutyryl-1-amidocyclohexane-1-carboxylic acid;

(c) methylene bis [4,4'-(2-chlorophenylureidophenoxyisobutyric acid)];

(d) 1,1-dimethylbiguanide; and (e) 5-aminosalicylic acid.

* * * * *

UNITED STATES PATENT AND TRADEMARK OFFICE
CERTIFICATE OF CORRECTION

PATENT NO. : 6,589,944 B1
DATED : July 8, 2003
INVENTOR(S) : Samuel Rahbar

It is certified that error appears in the above-identified patent and that said Letters Patent is hereby corrected as shown below:

Title page,
Item [54], Title, insert -- Novel -- before the word "Breakers."
Item [57], ABSTRACT,
Line 11, replace "5-arninosalicylic" with -- 5-aminosalicylic --.

Column 2,
Line 15, replace "Thomalley" with -- Thornalley --.

Column 3,
Line 23, replace "Yim etal." with -- Yim et al. --.

Column 8,
Line 49, replace "Tjemberg" with -- Tjernberg --.

Column 9,
Line 5, replace "p-AP" with -- β-AP --.
Line 29, replace "Tjemberg" with -- Tjernberg --.

Column 15,
Line 8, replace "Thomalley" with -- Thornalley --.
Line 12, replace "Tjemberg" with -- Tjernberg --.

Signed and Sealed this

Twentieth Day of July, 2004

JON W. DUDAS
*Acting Director of the United States Patent and Trademark Office*